(12) United States Patent
Hamana et al.

(10) Patent No.: US 6,388,154 B1
(45) Date of Patent: May 14, 2002

(54) PROCESS FOR PRODUCING STYRENE

(75) Inventors: Ryozo Hamana; Shohei Suzuki; Syuji Obayashi, all of Mie; Makoto Takiguchi; Hisashi Fujita, both of Ibaraki, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/462,482
(22) PCT Filed: Jul. 14, 1998
(86) PCT No.: PCT/JP98/03158
 § 371 Date: Jan. 18, 2000
 § 102(e) Date: Jan. 18, 2000
(87) PCT Pub. No.: WO99/03806
 PCT Pub. Date: Jan. 28, 1999

(30) Foreign Application Priority Data

Jul. 17, 1997 (JP) .............................................. 9-192118

(51) Int. Cl.$^7$ .......................... C07C 5/333; C07C 5/327
(52) U.S. Cl. ...................... 585/441; 585/435; 585/440; 585/444; 585/823
(58) Field of Search ................................. 585/435, 440, 585/441, 444, 823

(56) References Cited

U.S. PATENT DOCUMENTS 3,855,330 A * 12/1974 Mendelsohn et al. ........ 585/441
3,904,703 A * 9/1975 Lo et al. ...................... 585/441
4,691,071 A * 9/1987 Bricker ........................ 585/319
5,001,291 A * 3/1991 Holt et al. ................... 585/319
5,739,071 A * 4/1998 Chen et al. .................... 502/53

FOREIGN PATENT DOCUMENTS

JP 5-68885 A * 3/1993
JP 9-29095 A * 2/1997

* cited by examiner

Primary Examiner—Walter D. Griffin
(74) Attorney, Agent, or Firm—Oblon, Spivak, McClelland, Maier & Neustadt, P.C.

(57) ABSTRACT

A process for producing styrene by oxidative dehydrogentation of ethylbenzene, wherein the dehydrogenation of ethylbenzene is conducted through at least the following steps (1) to (3), whereby styrene can be produced in a high yield by controlling the lowering of the selectivity of an oxidation catalyst in hydrogen oxidation by removing an alkaline substance contained in the reaction mixture to be fed to step (2) beforehand:

step (1): a step of dehydrogenating ethylbenzene in the presence of a dehydrogenation catalyst to obtain a reaction mixture containing styrene and hydrogen;

step (2): a step of bringing the reaction mixture into contact with an oxidation catalyst to selectively oxidize the hydrogen contained in the mixture, thereby forming water;

step (3): a step of bringing the oxidized mixture into contact with a dehydrogenation catalyst to dehydrogenate the unreacted ethylbenzene contained in the mixture, thereby obtaining styrene.

9 Claims, 1 Drawing Sheet

PROCESS FOR PRODUCING STYRENE

TECHNICAL FIELD

The present invention relates to a process for producing styrene. More particularly, this invention relates to a process for producing styrene from ethylbenzene by the oxidative dehydrogenation method wherein the selectivity of an oxidation catalyst in hydrogen oxidation is prevented from lowering.

Styrene is an important compound as a starting material for polystyrene, synthetic rubbers, ABS resins, unsaturated polyester resins, etc.

BACKGROUND ART

Processes for producing styrene by the dehydrogenation reaction of ethylbenzene are known, as described in many documents so far. For example, a process employing an iron-potassium dehydrogenation catalyst is in industrial use.

However, since dehydrogenation reactions generally are considerably influenced by a reaction equilibrium, a high conversion cannot be obtained also in the case of ethylbenzene. Furthermore, when the dehydrogenation reaction of ethylbenzene is conducted in a heat-insulated reactor, the reaction temperature decreases with progress of the reaction because the dehydrogenation reaction is endothermic. This temperature decrease makes it more difficult to obtain a high conversion of ethylbenzene.

The so-called oxidative dehydrogenation method has hence been proposed in which an oxidation catalyst is used together with a dehydrogenation catalyst in the reaction process mainly for the purposes of (1) "shifting a reaction equilibrium" and (2) "compensating for the decrease in reaction temperature".

For example, Unexamined Published Japanese Patent Application No. sho. 60-130531 describes a method which comprises bringing a hydrocarbon susceptible to dehydrogenation into contact with a dehydrogenation catalyst comprising an iron compound and an alkaline metal, treating the resultant reaction mixture in the presence of an oxidation catalyst comprising a noble metal in Group 8 and tin to thereby selectively oxidize the hydrogen contained in the mixture, reheating the treated mixture to conduct dehydrogenation reaction again, and recovering the dehydrogenated hydrocarbon.

As a result of investigations made by the present inventors, the following has been found. In the oxidative dehydrogenation method involving the selective oxidation reaction of hydrogen, when the mixture of ethylbenzene, hydrogen, etc. to be fed to the oxidation catalyst contains alkaline substances, then the selectivity of the catalyst is impaired since the alkaline substances deposit on the catalyst. Because of this, the hydrocarbons including ethylbenzene burn on the oxidation catalyst, resulting in an increased amount of carbon dioxide yielded.

It is, for example, known that potassium compounds are contained in ethylbenzene dehydrogenation catalysts and that such potassium compounds fly off during the dehydrogenation reaction (B. D. Herzog et. al., *Ind. Eng. Chem. Prod. Res. Dev.* 23, (2), 187(1984); Hayasaka et. al., *Dai 24-kai Nippon Hokozoku Kogyokai Taikai Yoshi-shu*, p.36 (1990); etc.).

If those potassium compounds fly off in a process in which dehydrogenation and the selective oxidation of hydrogen are alternately conducted in series, the oxidation catalyst comes to have considerably impaired selectivity.

On the other hand, carbon dioxide is known to serve to reduce the dehydrogenation activity of dehydrogenation catalysts (Hirano, *Shokubai,* 29, (8), 641 (1987), etc.). Consequently, an increase in the amount of carbon dioxide yielded in the oxidation step is undesirable for the subsequent dehydrogenation reaction because it means a suppression in conversion in the downstream dehydrogenation reaction.

An object of the present invention is to provide a method for preventing the hydrogen oxidation selectivity of an oxidation catalyst from lowering in a process which comprises conducting the dehydrogenation reaction of ethylbenzene to yield a reaction mixture containing styrene and hydrogen, burning the hydrogen by selective oxidation reaction, and further subjecting the unreacted ethylbenzene contained in the mixture to dehydrogenation reaction to produce styrene.

DISCLOSURE OF THE INVENTION

The present inventors made intensive investigations in order to eliminate the above problem. As a result, they have found that the oxidation reaction of hydrogen can be caused to proceed without impairing the selectivity of a catalyst for selective hydrogen oxidation, by removing alkaline substances contained in a slight amount in a dehydrogenation reaction product when the reaction product is located downstream from a layer of an ethylbenzene dehydrogenation reaction catalyst and upstream from a layer of the catalyst for the selective oxidation of hydrogen contained in the dehydrogenation reaction product. The present invention has been completed based on this finding.

The essential point of the present invention resides in a process for producing styrene by the dehydrogenation reaction of ethylbenzene which comprises at least the following steps (1) to (3):

step (1): a step of dehydrogenating ethylbenzene in the presence of a dehydrogenation catalyst to obtain a reaction mixture containing styrene and hydrogen;

step (2): a step of bringing the reaction mixture into contact with an oxidation catalyst to selectively oxidize the hydrogen contained in the mixture into water;

step (3): a step of bringing the oxidized mixture into contact with a dehydrogenation catalyst to dehydrogenate the unreacted ethylbenzene contained in the mixture, thereby to obtain styrene, characterized in that an alkaline substance contained in the reaction mixture to be fed to step (2) is removed from the mixture beforehand.

BEST MODES FOR CARRYING OUT THE INVENTION

Figure 1:
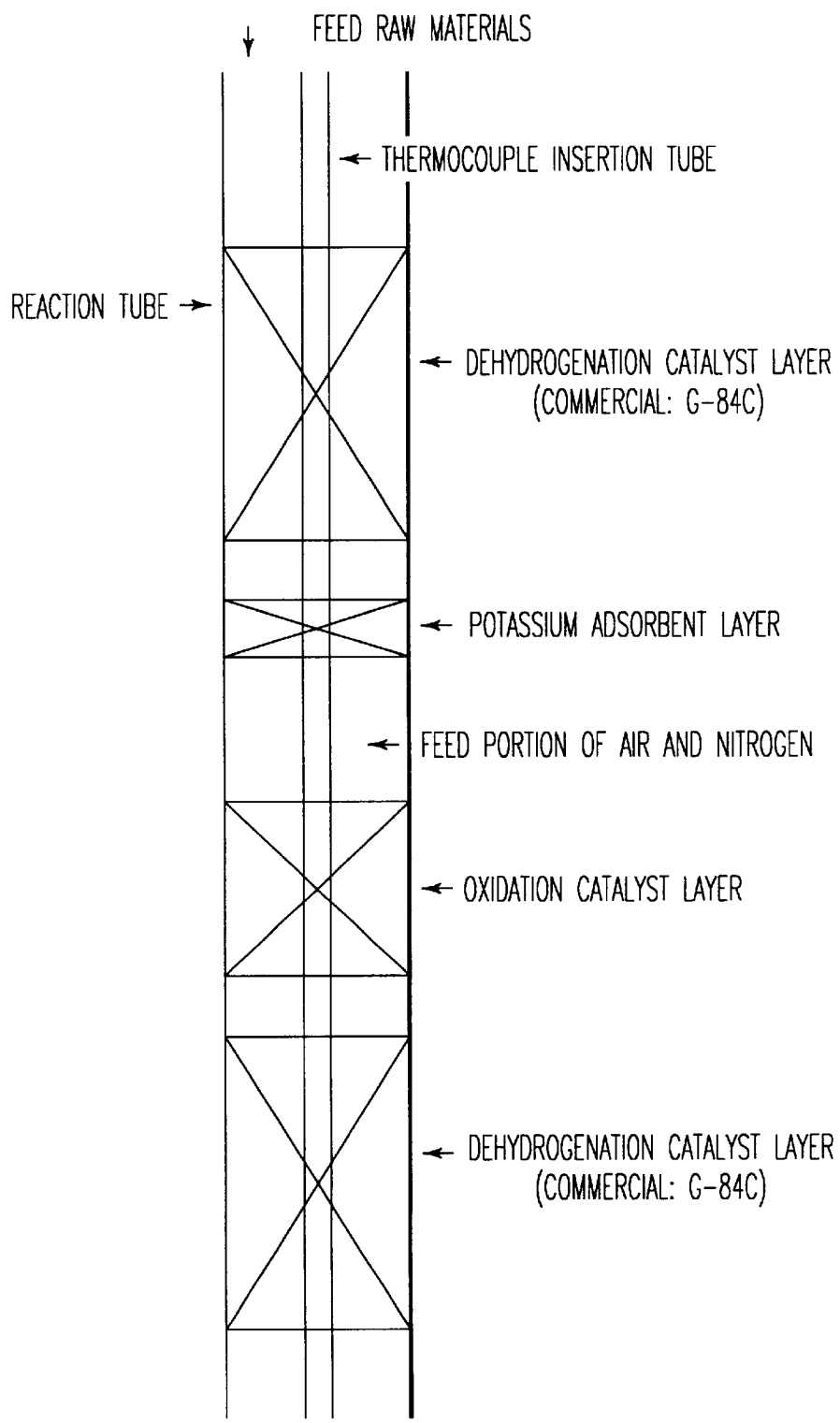
FIG. 1 is a vertical sectional view of a reaction tube used in the Examples according to the present invention.

The present invention will be explained below in detail.

The process for producing styrene used in the present invention is, for example, as follows.

In the Case of "Dehydrogenation Reaction+Oxidation Reaction+Dehydrogenation Reaction":

Ethylbenzene (which may contain styrene) is passed through a first dehydrogenation reactor (catalyst layer) at a temperature of from 500 to 700° C. and a pressure of from 4.9 to 981 kPa to conduct dehydrogenation reaction and thereby obtain a mixture comprising styrene, hydrogen, unreacted ethylbenzene, etc. The mixture obtained is passed through an oxidation reactor (catalyst layer) to selectively oxidize the hydrogen with a freshly introduced oxygen-containing gas in the presence of a catalyst for selective hydrogen oxidation. Furthermore, the mixture discharged from this oxidation reactor (catalyst layer) is passed through a downstream dehydrogenation reactor (catalyst layer) to dehydrogenate the unreacted ethylbenzene and thereby obtain styrene. In this process, the hydrogen undergoes internal combustion in the oxidation reactor, and this not only elevates the temperature of the mixture due to the resultant heat generation but results in a diminution of hydrogen due to the oxidation (burning). Because of this, there is an advantage that the inhibition of the downstream dehydrogenation reaction by an equilibrium is reduced.

In the above process, an alkaline substance contained in a slight amount in the dehydrogenation reaction product is removed after the step of the dehydrogenation reaction of ethylbenzene, i.e., when the reaction product is located downstream from the dehydrogenation reaction catalyst layer, and before the step of the selective oxidation reaction of the hydrogen contained in the dehydrogenation reaction product, i.e., when the reaction product is located upstream from the selective-oxidation reaction catalyst layer. Hence, the catalyst layer for selective hydrogen oxidation reaction has improved selectivity in hydrogen oxidation reaction. As a result, the other hydrocarbons can be inhibited from burning and thus causing an increase in yielded carbon dioxide amount. Consequently, a high conversion can be obtained in the dehydrogenation reaction in the dehydrogenation reaction catalyst layer disposed after the oxidation reaction catalyst layer.

In a preferred method, water vapor is incorporated into the ethylbenzene to be fed. Water vapor is said to reduce, in the dehydrogenation reaction, the partial pressures of ethylbenzene and the styrene being yielded and to inhibit coke generation. Although there are no particular limitations on the proportion of water vapor to ethylbenzene, the molar ratio of the water vapor to be fed to the ethylbenzene is preferably 15 or lower, more preferably from 1 to 14.

If desired and necessary, the dehydrogenation reactors (catalyst layers) and the hydrogen oxidation reactor (catalyst layer) may be arranged in a larger number of stages in carrying out the reactions. It is, of course, necessary to conduct the removal of an alkaline substance between these dehydrogenation reactors (catalyst layers) and these oxidation reactors (catalyst layers). However, combinations each containing five or more dehydrogenation reactors (catalyst layers) are impractical because the investment required is too large for the effect obtained.

Preferred examples of the ethylbenzene dehydrogenation catalyst for use in the present invention include "a dehydrogenation catalyst comprising an iron compound and an alkaline metal selected from the group consisting of the Group 1A and Group 2A elements of the periodic table" as described, e.g., in Unexamined Published Japanese Patent Application No. Sho. 60-130531, cited above. The term "alkaline metal" as used in this specification means any of the Group 1A and Group 2A metals of the periodic table including lithium, sodium, potassium, rubidium, cesium, beryllium, magnesium, calcium, strontium, and barium. In a preferred embodiment of the present invention, the dehydrogenation catalyst may contain one or more of the Group 4B, Group 5B, and Group 6B metals of the periodic table. A catalyst "consisting mainly of an iron oxide and potassium oxide" as described in Unexamined Published Japanese Patent Application No. Hei. 4-277030 is also included in the preferred examples. A preferred composition of the dehydrogenation catalyst for use in the process of the present invention consists substantially of from 70 to 80% by weight ferric oxide and from 10 to 20% by weight potassium oxide and may contain a small amount of other ingredients.

Examples of the catalyst for selective hydrogen oxidation to be used in the present invention include: a catalyst comprising at least one metal selected from the Group 4, Group 5, and Group 8 metals of the periodic table; and a catalyst comprising both of at least one metal selected from the Group 4 and Group 5 metals of the periodic table and at least one metal selected from the Group 8 metals of the periodic table. Specific examples thereof include "an oxidation catalyst comprising a noble metal in Group 8 of the periodic table and tin and, more preferably, an oxidation catalyst comprising a noble metal in Group 8 of the periodic table and tin and deposited on an inorganic support having a surface area in the range of from 1 to 500 $m^2/g$" as described in Unexamined Published Japanese Patent Application No. Sho. 60-130531, cited above, and "an oxidation catalyst comprising a Group 8 noble metal, a Group 4A metal, and a Group 1A or Group 2A metal and, more preferably, an oxidation catalyst comprising a Group 8 noble metal, a Group 4A metal, and a Group 1A or Group 2A metal and deposited on an aluminum support burned at a temperature in the range of about from 900 to 1,500° C." as described in Unexamined Published Japanese Patent Application No. Sho. 61-225140. Also usable as preferred catalysts are "a catalyst containing tin or containing tin and an alkali metal" as described in Unexamined Published Japanese Patent Application No. Hei. 6-298678 and a catalyst containing a Group 4 or Group 5 metal of the periodic table, e.g., tin, titanium, tantalum, niobium, etc., and a Group 8 metal of the periodic table, e.g., platinum or palladium, such as that described in Unexamined Published Japanese Patent Application No. Hei. 9-29095.

The alkaline substances which fly out of dehydrogenation catalysts have not been specified. However, they are presumed to be, for example, the carbonates of alkaline metals, e.g., potassium carbonate, the hydroxides of alkaline substances, e.g., potassium hydroxide, or the like, because they generate in the presence of high-temperature water vapor and carbon dioxide.

The term "alkaline substances" as used herein is a general term for compounds of alkaline metals, such as the oxides, carbonates, and hydroxides of the aforementioned alkaline metals.

To remove an alkaline substance in the present invention means that the content of the alkaline substance in the reaction mixture to be fed to step (2) is reduced to such a degree that step (2) can be continuously conducted stably without causing deterioration of the oxidation reaction catalyst.

Examples of methods for removing such alkaline substances include a method in which a removal layer for removing alkaline substances which comprises a dust collector, e.g., a cyclone, bag filter, or scrubber, is disposed between step (1) and step (2) and a method in which an adsorption layer comprising an adsorbing apparatus having a fixed, moving, fluidized, or other bed of an adsorbent is disposed. The term "between step (1) and step (2)" means anywhere between a location immediately downstream from the ethylbenzene dehydrogenation catalyst layer in step (1) and a location immediately upstream from the catalyst layer in the subsequent step (2) for the selective oxidation of the hydrogen contained in the dehydrogenation reaction mixture.

The adsorption layer means a layer comprising an adsorbent which physically or chemically adsorbs the alkaline substances. The adsorbent is not particularly limited as long as it is a substance having the property of adsorbing the alkaline substances. Specific examples thereof include silica compounds, alumina compounds, compounds (called ceramics) obtained by burning silica-alumina mixtures at a high temperature, inorganic oxides (alone), e.g., iron oxides, titanium dioxide, calcium oxide, and magnesium oxide, mixtures of two or more thereof, and composites of these. The adsorbent may be composed of moldings of any shape such as, e.g., moldings in a ball or honeycomb shape, extruded moldings (in the shape of cylinder, pipe, etc.), or moldings of irregular shapes.

The use amount of an adsorbent is not particularly limited. However, it is generally desirable that an adsorbent be used in an amount in the range of from 0.001 to 2 times by volume, preferably from 0.005 to 1 time by volume, the amount of the dehydrogenation catalysts. Even if an adsorbent is used in an amount exceeding the upper limit, not only the effect thereof is not enhanced but the equipment disadvantageously needs to have a larger size, resulting in an increased equipment cost. On the other hand, if the adsorbent amount is smaller than the lower limit, breakthrough comes to occur in a short period, resulting in a shortened period of stable operation.

EXAMPLES

The present invention will be explained below in more detail by reference to Examples, but the invention should not be construed as being limited to these Examples unless the invention departs from the spirit thereof.

EXAMPLE 1

An oxidation catalyst was produced according to the Example 1 given in Unexamined Published Japanese Patent Application No. Hei. 9-29095.

The detailed procedure is as follows. First, 44.1 g of concentrated nitric acid and 7.6 g of tin chloride were added to 623.6 g of water. The solution obtained was gradually added to 1,139.6 g of hydrated α-alumina over 15 seconds with stirring and the resultant mixture was then vigorously agitated for 5 minutes. The gel thus obtained was extruded with an extruder and the extrudate was dried in an oven at 95° C. for 2 hours. The above operation was repeated. The oven-dried extrudate thus obtained in an amount of 2,943 g was burned at 350° C. for 1 hour and further at 600° C. for 3 hours and then allowed to cool gradually to room temperature. In a dry atmosphere, 535 g of the burned extrudate was heated to a temperature of 1,040° C. over 6 hours, subsequently kept at this temperature for 3 hours, and then allowed to cool gradually to room temperature over 6 hours. Subsequently, 12.9 g of a chloroplatinic acid solution containing 2.54 wt % platinum, 37.3 g of a lithium nitrate solution containing 0.88 wt % lithium, and 7.3 g of concentrated nitric acid were added to 142.5 g of water, and this mixture was transferred to a glass evaporator with stirring. To this solution was added 163.6 g (200 cc) of the burned extrudate to conduct impregnation at 95° C. The impregnated extrudate was dried in an oven at a temperature of 150° C. for 2 hours, subsequently burned in a quartz pipe at a temperature of 650° C. for 2 hours, and then cooled to room temperature. Thus, a Pt—Sn oxidation catalyst was obtained.

(Reactions)

A reaction tube having an inner diameter of 21 mm equipped with a thermocouple insertion tube having an outer diameter of 6 mm was packed with 36 cc of a commercial dehydrogenation catalyst (Nissan Girdler Catalyst; G-84C) and, under the catalyst, with 10 cc of commercial silica-alumina ceramic balls 1 (manufactured by Chipton Co.; 3-mm spheres) as an adsorbent for alkaline substances, as shown in FIG. 1. The reaction tube was further packed, under the adsorbent, with 21 cc of the oxidation catalyst described above and, under this oxidation catalyst, with 36 cc of the same dehydrogenation catalyst as the above. While temperature control was conducted with a divided heater, the inlet temperature of the dehydrogenation catalyst was elevated to 600° C. in a nitrogen stream. Subsequently, reactions were initiated by introducing a styrene/ethylbenzene mixture, water, and hydrogen into an upper part of the reaction tube and further introducing an air/nitrogen mixed gas into a part under the adsorbent for alkaline substances. During the reactions, the dehydrogenation catalyst layers and the adsorbent layer were kept at an almost constant temperature around 600° C. The temperature increase in the oxidation catalyst layer was 30 to 40° C. The feed materials fed to the catalyst layers as a whole had the following composition.

styrene/ethylbenzene/water/hydrogen/oxygen/nitrogen=0.4/1/11.5/ 0.36–0.48/0.18/2.05 (by mole)

The pressure was 65 kPa, and the LHSV of the styrene/ethylbenzene mixture based on the dehydrogenation catalyst was 2.0/hr.

After initiation of the reactions, the liquid and gas were sampled at the outlet of each catalyst layer and at the outlet of the reaction tube. Each sample was analyzed with a gas chromatograph to determine the composition. The results obtained are shown in Table 1.

EXAMPLE 2

The same procedure as in Example 1 was conducted, except that commercial silica-alumina ceramic balls 2 (manufactured by Chipton Co.; differing from ceramic balls 1 in silica/alumina proportion) were used as an adsorbent. The results obtained are shown in Table 1.

COMPARATIVE EXAMPLE 1

The same procedure as in Example 1 was conducted, except that no adsorbent was packed. The results obtained are shown in Table 1.

These Examples of reactions show that in the processes using an adsorbent according to the present invention, the amount of yielded carbon dioxide did not increase and the second dehydrogenation catalyst layer stably retained its activity.

Table 1 Results of Reactions

Upper numeral: carbon dioxide concentration in outlet gas (vol %)

Lower numeral: conversion of ethylbenzene in second dehydrogenation catalyst layer (wt %)

| Example | Adsorbent | Reaction period (hr) | | | |
| --- | --- | --- | --- | --- | --- |
| | | 50 | 250 | 500 | 800 |
| Example 1 | ceramic balls 1 | 1.2 50 | 1.3 47 | 1.2 45 | 1.2 45 |

-continued

| Example | Adsorbent | Reaction period (hr) | | | |
|---|---|---|---|---|---|
| | | 50 | 250 | 500 | 800 |
| Example 2 | ceramic balls 2 | 1.3 48 | 1.3 47 | 1.3 45 | 1.3 45 |
| Comparative Example 1 | none | 1.5 43 | 2.4 28 | 2.9 20 | 3.2 18 |

Possibility of Industrial Application

As described above, when the process of the present invention is used, the oxidation catalyst can be prevented from being poisoned by the flying of alkaline substances, whereby the selectivity of the oxidation catalyst is kept stable without being reduced. Because of this, the hydrocarbons including styrene and ethylbenzene are inhibited from burning and thus causing an increase in yielded carbon dioxide amount. As a result, the dehydrogenation catalyst disposed after the oxidation catalyst layer is also prevented from suffering an activity lowering with time. Furthermore, since the multistage dehydrogenation reaction undergoes no decrease in reaction temperature and is less influenced by an equilibrium, the process as a whole can produce styrene in an exceedingly high yield as compared with cases where no adsorbent is used.

What is claimed is:

1. A process for producing styrene by dehydrogenation of ethylbenzene, comprising:
    (1) dehydrogenating ethylbenzene in the presence of a dehydrogenation catalyst to obtain a reaction mixture containing styrene and hydrogen;
    (2) contacting the reaction mixture with an oxidation catalyst to selectively oxidize the hydrogen contained in the mixture, thereby forming water;
    (3) contacting the oxidized mixture with a dehydrogenation catalyst to dehydrogenate an unreacted ethylbenzene contained in the mixture, thereby obtaining styrene,
    wherein an alkaline substance contained in the reaction mixture is removed before contacting said reaction mixture with said oxidation catalyst.

2. The process for producing styrene according to claim 1, wherein the alkaline substance is a potassium compound.

3. The process for producing styrene according to claim 1, wherein each dehydrogenation catalyst used in steps (1) and (3) comprises an iron compound and an alkaline metal of Group 1A or an alkaline earth metal of Group 2A of the Periodic Table.

4. The process for producing styrene according to claim 3, wherein each dehydrogenation catalyst comprises an iron oxide and potassium oxide.

5. The process for producing styrene according to claim 1, wherein the oxidation catalyst used in step (2) comprises at least one metal selected from Group 4, Group 5, and Group 8 metals of the Periodic Table.

6. The process for producing styrene according to claim 1, wherein the oxidation catalyst used in step (2) comprises both of at least one metal selected from Group 4 and Group 5 metals of the Periodic Table and at least one metal selected from Group 8 metals of the Periodic Table.

7. The process for producing styrene according to claim 1, wherein the removal of the alkaline substance is conducted by providing an alkaline-substance removal layer disposed between step (1) and step (2).

8. The process for producing styrene of claim 7, wherein the alkaline-substance adsorption layer comprises at least one adsorbent selected from the group consisting of a silica compound, an alumina compound, and a silica-alumina composite compound.

9. The process for producing styrene according to claim 8, wherein the adsorbent is used in an amount of from 0.001 to 2 times by volume of the amount of the dehydrogenation catalysts of steps (1) and (2).

* * * * *